United States Patent
Kondo et al.

(10) Patent No.: US 8,557,586 B2
(45) Date of Patent: Oct. 15, 2013

(54) CELLULOSE DEGRADABLE YEAST AND METHOD FOR PRODUCTION THEREOF

(75) Inventors: Akihiko Kondo, Kobe (JP); Ryosuke Yamada, Kobe (JP); Hideo Noda, Amagasaki (JP)

(73) Assignees: National University Corporation Kobe University, Hyogo (JP); Kansai Chemical Engineering Co., Ltd., Hyogo (JP); Bio-Energy Corporation, Hyogo (JP)

( * ) Notice: Subject to any disclaimer, the term of this patent is extended or adjusted under 35 U.S.C. 154(b) by 91 days.

(21) Appl. No.: 12/964,808

(22) Filed: Dec. 10, 2010

(65) Prior Publication Data

US 2012/0149116 A1  Jun. 14, 2012

(51) Int. Cl.
C12N 1/22  (2006.01)
C12N 15/81  (2006.01)

(52) U.S. Cl.
USPC ................................ 435/471; 435/254.2

(58) Field of Classification Search
None
See application file for complete search history.

(56) References Cited

U.S. PATENT DOCUMENTS

2010/0075363 A1* 3/2010 McBride et al. .............. 435/29

FOREIGN PATENT DOCUMENTS

| JP | 2008-086310 | | 4/2008 |
|---|---|---|---|
| WO | WO 01/79483 A1 | | 10/2001 |
| WO | WO2008/064314 | * | 5/2008 |

OTHER PUBLICATIONS

Brachmann et al., "Designer deletion strains derived from *Saccharomyces cerevisiae* S288C: a useful set of strains and plasmids for PCR-mediated disruption and other applications" *Yeast*, vol. 14, pp. 115-132 (1998).

Choi et al., "Construction of an industrial polyploid strain of *Saccharomyces cerevisiae* containing Saprolegnia fera β-amylase gene a secreting β-amylase", *Biotechnology Letters*, vol. 24, pp. 1785-1790 (2002).

Fujita et al., "Synergistic Saccharification, and direct fermentation to ethanol, of amorphous cellulose by use of an engineered yeast strain codisplaying three types of cellulolytic enzyme" *Applied and Environmental Microbiology*, vol. 70, No. 2, pp. 1207-1212 (2004).

Haan et al., "Hydrolysis and fermentation of amorphous cellulose by recombinant *Saccharomyces cerevisiae*" *Metabolic Engineering*, vol. 9, pp. 87-94 (2007).

Lee et al., "Improved efficiency and stability of multiple cloned gene insertions at the δ sequences of *Saccharomyces cerevisiae*" *Applied Microbiol Biotechnol*, vol. 48, pp. 339-345 (1997).

Lee et al., "Sequential δ-integration for the regulated insertion of cloned genes in *Saccharomyces cerevisiae*" *Biotechnol. Prog.*, vol. 13, pp. 368-373 (1997).

Matsumoto et al., "Construction of yeast strains with high cell surface lipase activity by using novel display systems based on the Flo1p flocculation functional domain" *Applied and Environmental Microbiology*, vol. 68, No. 9, pp. 4517-4522 (2002).

Parekh et al., "An integrating vector for tunable, high copy, stable integration into the dispersed Ty δ sites of *Saccharomyces cerevisiae*" *Biotechnol. Prog.*, vol. 12, pp. 16-21 (1996).

Sato et al., "Long anchor using Flo1 protein enhances reactivity of cell surface-displayed glucoamylase to polymer substrates" *Appl. Microbiol. Biotechnol.*, vol. 60, pp. 469-474 (2002).

Tsai et al., "Functional assembly of minicellulosomes on the *Saccharomyces cerevisiae* cell surface for cellulose hydrolysis and ethanol production" *Applied and Environmental Microbiology*, vol. 75, No. 19, pp. 6087-6093 (2009).

Wen et al., "Yeast surface display of trifunctional minicellulosomes for simultaneous Saccharification and fermentation of cellulose to ethanol" *Applied and Environmental Microbiology*, vol. 76, No. 4, pp. 1251-1260 (2010).

Yamada et al., "Cocktail δ-integration: a novel method to construct cellulolytic enzyme expression ratio-optimized yeast strains" *Microbial Cell Factories*, 9:32 (2010).

Yamada et al., "Novel strategy for yeast construction using δ-integration and cell fusion to efficiently produce ethanol from raw starch" *Appl. Microbiol. Biotechnol.*, vol. 85, pp. 1491-1498 (2010).

Yanase et al., "Ethanol production from cellulosic materials using cellulose-expressing yeast", *Biotechnol. J.*, vol. 5, pp. 449-455 (2010).

* cited by examiner

*Primary Examiner* — Tekchand Saidha
*Assistant Examiner* — MD. Younus Meah
(74) *Attorney, Agent, or Firm* — Alchemy-Partners, PC

(57) ABSTRACT

The present invention provides a method for producing a cellulose degradable yeast, comprising the step of co-introducing genes coding for at least two cellulose-degrading enzymes into a yeast host via integration with a yeast δ sequence. According to the invention, a yeast having an improved cellulose degradation ability are provided.

20 Claims, 8 Drawing Sheets

1. MT8-1/IBEC2 (ordinary integration)
2. MT8-1/δBEC (ordinary δ integration)
3. MT8-1/cocδBEC1 (1-cycle cocktail δ integration)
4. MT8-1/cocδBEC2 (2-cycle cocktail δ integration)
5. MT8-1/cocδBEC3 (3-cycle cocktail δ integration)
6. MT8-1 (Wild strain)

1. MT8-1/IBEC2 (ordinary integration)
2. MT8-1/δBEC (ordinary δ integration)
3. MT8-1/cocδBEC1 (1-cycle cocktail δ integration)
4. MT8-1/cocδBEC2 (2-cycle cocktail δ integration)
5. MT8-1/cocδBEC3 (3-cycle cocktail δ integration)
6. MT8-1 (Wild strain)

US 8,557,586 B2

CELLULOSE DEGRADABLE YEAST AND METHOD FOR PRODUCTION THEREOF

BACKGROUND OF THE INVENTION

1. Field of the Invention

The present invention relates to a cellulose degradable yeast and a production method therefor.

2. Description of the Related Art

Fermentation microorganisms that originally cannot metabolize principal components of soft-biomass, such as cellulose, hemicellulose, and the like have been modified using bioengineering methods as an attempt to attain ethanol fermentation directly from non-edible carbon sources. Cell surface-displaying techniques are suitably used as such bioengineering methods. For example, yeasts that display on the surface a group of enzymes (i.e., a plurality of enzymes) that hydrolyze cellulose have been produced by cell surface-displaying techniques (for example, WO 01/79483 and Japanese Laid-Open Patent Publication No. 2008-86310).

Originally, organisms regulate the level of protein expression in various processes such as transcription, translation, and the like. However, it is very difficult to control the levels and balance of expression of a plurality of foreign proteins in the foreign gene expression system of a yeast with genetically modified.

In conventional researches, it has been common that the expression level of foreign-gene is regulated by selecting the type of promoter. However, such a regulation depends on various factors such as the gene to be expressed, the kind of host yeast strain, the culture conditions, and like, making precise control or extensive application difficult, and it has not been possible to determine the optimal expression level.

It is known that, for example, a filamentous fungus *Trichoderma reesei* or the like, which is known to efficiently degrade cellulose, retains a very large variety of cellulase genes and precisely controls the balance of their expression depending on the environment. However, when those genes are heterologously expressed in different microorganisms such as yeast, it is very difficult to control the balance of their expression.

The δ integration system is known as a technique that can introduce multiple copies of a gene by homologous recombination with δ sequences present in large numbers on a yeast chromosome (for example, *Appl. Microbiol. Biotechnol.,* 1997, Vol. 48, pp. 339-345; *Biotechnology Letters,* 2002, Vol. 24, pp. 1785-1790; *Biotechnol. Prog.,* 1996, Vol. 12, pp. 16-21; *Biotechnol. Prog.,* 1997, Vol. 13, pp. 368-373). These documents relate to that the introduction of multiple copies of a single expression gene to be expressed using integration with yeast δ sequences can result in increase in the level or improved efficiency of its expression, or can make the expression stable.

SUMMARY OF THE INVENTION

An object of the present invention is to provide a yeast with improved cellulose degradation.

The present invention provides a method for producing a cellulose degradable yeast, comprising the step of co-introducing genes coding for at least two cellulose-degrading enzymes into a yeast host via integration with a yeast δ sequence.

In one embodiment, the at least two cellulose-degrading enzymes are a combination of enzymes that hydrolyze cellulose in different ways.

In a further embodiment, the combination of enzymes that hydrolyze cellulose in different ways is a combination of enzymes selected from a group consisting of endoglucanase, cellobiohydrolase, and β-glucosidase.

In a more further embodiment, the combination of enzymes that hydrolyze cellulose in different ways is a combination of endoglucanase, cellobiohydrolase, and β-glucosidase.

In a different embodiment, the cellulose-degrading enzymes are designed to be displayed on a cell surface.

In a still different embodiment, the step of co-introduction is repeated twice or more.

The present invention also provides a yeast which contains genes coding for at least two cellulose-degrading enzymes that hydrolyze cellulose in different ways, wherein the enzymes are a combination of (A) endoglucanase and (B) β-glucosidase, and the ratio for genes of (A)/(B) is 2 or greater.

The present invention also provides a yeast which contains genes coding for at least two cellulose-degrading enzymes that hydrolyze cellulose in different ways, wherein the enzymes are a combination of (A) endoglucanase and (B) cellobiohydrolase, and the ratio for genes of (A)/(B) is 1 or greater.

The present invention also provides a yeast which contains genes coding for at least three cellulose-degrading enzymes that hydrolyze cellulose in different ways, wherein the enzymes are a combination of (A) endoglucanase, (B) β-glucosidase, and (C) cellobiohydrolase, and the ratio for genes of (A)/(B) is 2 or greater and the ratio for genes of (A)/(C) is 1 or greater.

According to the present invention, a yeast having an improved cellulose degradation ability and a production method therefor are provided.

Figure 1:
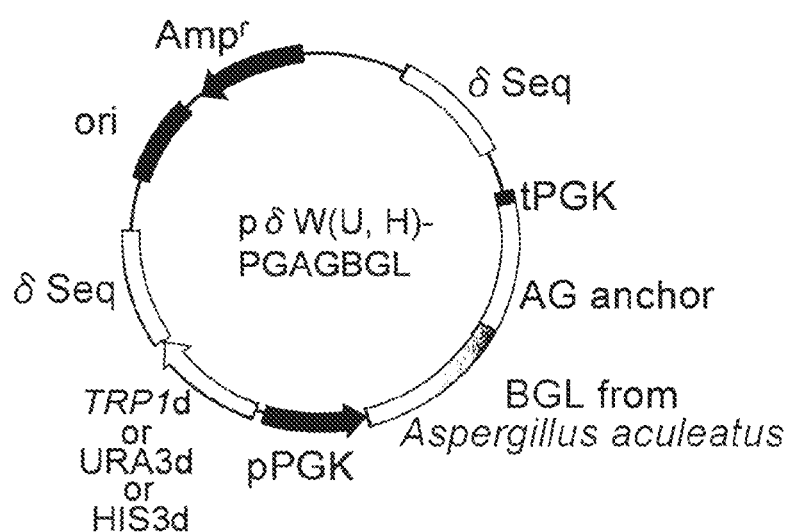
FIG. 1 is a schematic drawing showing the vector configuration of pδW-PGAGBGL, pδU-PGAGBGL, and pδH-PGAGBGL.

BEC1 strain, MT8-1/cocδBEC2 strain, an MT8-1/cocδBEC3 strain, an MT8-1/IBEC2 strain, and a wild strain.

DESCRIPTION OF THE PREFERRED EMBODIMENTS

It is reported that yeast δ sequences are long terminal repeats of retrotransposons Ty1 and Ty2 for *Saccharomyces cerevisiae* (for example, *Appl. Microbiol. Biotechnol.,* 1997, Vol. 48, pp. 339-345; *Biotechnology Letters,* 2002, Vol. 24, pp. 1785-1790; *Biotechnol. Prog.,* 1996, Vol. 12, pp. 16-21; *Biotechnol. Prog.,* 1997, Vol. 13, pp. 368-373), also referred to as Ty sequence. The δ sequence is known and readily available to those skilled in the art (Genebank Accession Number M18706). For example, a δ sequence pair of 5' sequence and 3' sequence may be prepared so as to enable homologous recombination with δ sequences present in large numbers on a yeast chromosome. For example, such a δ sequence pair may be prepared by designing a primer pair based on the information of the δ sequence and carrying out PCR amplification with the genomic DNA of the yeast as a template (for example, Preparation Example 3 below). In the present invention, commercially available δ integration vectors may also be used.

A cellulose-degrading enzyme refers to any enzyme that can cleave β1,4-glucosidic linkage, to which is also referred simply as "cellulase" herein. It may be derived from any cellulose hydrolase-producing bacterium. Typical examples of cellulose hydrolase-producing bacteria include microorganisms belonging to the genus *Aspergillus* (for example, *Aspergillus aculeatus, Aspergillus niger,* and *Aspergillus oryzae*), the genus *Trichoderma* (for example, *Trichoderma reesei*), the genus *Clostridium* (for example, *Clostridium thermocellum*), the Cellulomonas (for example, *Cellulomonas fimi* and *Cellulomonas uda*), the genus *Pseudomonas* (for example, *Pseudomonas fluorescence*), and the like.

Hereinbelow, description is given with regard to endoglucanase, cellobiohydrolase, and β-glucosidase for typical cellulose-degrading enzymes, but cellulose-degrading enzymes are not limited thereto.

Endoglucanase is an enzyme, which may be usually referred to as cellulase, that intramolecularly cleaves cellulose to generate glucose, cellobiose, and cello-oligosaccharide ("intramolecular cellulose cleaving"). There are five kinds of endoglucanase and referred to as endoglucanase I, endoglucanase II, endoglucanase III, endoglucanase IV, and endoglucanase V, respectively. They are distinguished by the difference in amino acid sequence but have in common the action of intramolecular cellulose cleaving. For example, endoglucanase derived from *Trichoderma reesei* (especially EGII) may be used, but endoglucanase is not limited thereto.

Cellobiohydrolase degrades cellulose from either the reducing terminal or the nonreducing terminal thereof to release cellobiose ("cellulose molecule terminal cleaving"). There are two kinds of cellobiohydrolase and are referred to as cellobiohydrolase I and cellobiohydrolase II, respectively. They are distinguished by the difference in amino acid sequence but have in common the action of cellulose molecule terminal cleaving. For example, cellobiohydrolase derived from *Trichoderma reesei* (especially CBHII) may be used, but cellobiohydrolase is not limited thereto.

β-Glucosidase is an exo-hydrolase that liberates glucose units from the nonreducing terminal of cellulose ("glucose unit cleaving"). β-Glucosidase can cleave the β1,4-glucosidic linkage between aglycon or a sugar chain and β-D-glucose, and hydrolyze cellobiose or cello-oligosaccharide to generate glucose. β-Glucosidase is a typical example of an enzyme that can hydrolyze cellobiose or cello-oligosaccharide. There is currently one type of β-glucosidase known which is called β-glucosidase 1. For example, β-glucosidase derived from *Aspergillus* aculeatus (especially BGL1) may be used, but β-glucosidase is not limited thereto.

For favorable cellulose hydrolysis, it is preferable to combine enzymes that hydrolyze cellulose in different ways. Enzymes that act in different ways to hydrolyze cellulose, such as intramolecular cellulose cleaving, cellulose molecule terminal cleaving, and glucose unit cleaving, may be suitably combined. Examples of enzymes that have respective ways of hydrolysis include, but are not limited to, endoglucanase, cellobiohydrolase, and β-glucosidase. A combination of enzymes that have different ways of hydrolyzing cellulose may be selected from the group consisting of, for example, endoglucanase, cellobiohydrolase, and β-glucosidase. Since it is desirable that glucose, which is a constituent sugar of cellulose, is eventually produced, it is preferable that at least one enzyme that can generate glucose is included. Regarding the enzyme that can generate glucose, not only glucose unit cleaving enzymes (for example, β-glucosidase), but endoglucanase can also generate glucose. Preferably, β-glucosidase, endoglucanase, and cellobiohydrolase may be expressed in a yeast.

The gene of an enzyme to be expressed can be obtained from a microorganism that produces the enzyme by PCR or hybridization with primers or a probe designed based on known sequence information. Also, the enzyme gene may be excised from an existing vector that contains it, preferably in the form of an expression cassette, for the use thereof.

The enzyme gene can be used to construct an expression cassette. The expression cassette may contain so-called regulatory factors such as an operator, a promoter, a terminator, and an enhancer that regulate the expression of the gene. The promoter and the terminator may be those of the gene to be expressed, or those derived from a different gene may be used. For the promoter and the terminator, promoters and terminators of GAPDH (glyceraldehyde 3'-phosphate dehydrogenase), PGK (phosphoglycerate kinase), GAP (glyceraldehyde 3'-phosphate), and like may be used, but the selection of a promoter and a terminator may depend on the expression of the enzyme gene of interest and they can be suitably selected by those skilled in the art. Additional factors that regulate the expression (such as an operator and an enhancer) or the like may be contained as necessary. Expression regulatory factors such as operators and enhancers may also be suitably selected by those skilled in the art. The expression cassette may further contain a necessary functional sequence depending on the purpose of the expression of the gene. The expression cassette may contain linkers as necessary.

For the expression of an enzyme for yeast surface display, a cell surface engineering technique may be used. Examples include, although they are not limited to, (a) displaying an enzyme on the cell surface via the GPI anchor of a cell surface-localized protein, (b) displaying an enzyme on the cell surface via the sugar chain binding domain of a cell surface-localized protein, and (c) displaying an enzyme on the cell surface via a periplasm protein (another receptor molecule or target receptor molecule). Relevant techniques for cell surface engineering are described also in, for example, WO 01/79483 and Japanese Laid-Open Patent Publication No. 2008-86310.

Examples of usable cell surface-localized proteins include α- or a-agglutinin, which is a yeast flocculation protein (for use as the GPI anchor); Flo1 proteins (Flo1 proteins can be used as the GPI anchor with modification of amino acid length on the N-terminal; for example, Flo42, Flo102, Flo146, Flo318, Flo428, and the like; *Appl. Microbiol. Biotechnol.*, 2002, Vol. 60, pp. 469-474: Note that Flo1326 refers to the full-length Flo1 protein); Flo proteins (there are no GPI anchor functions and flocculability is used, Floshort or Flolong; *Applied and Environmental Microbiology*, 2002, Vol. 68, pp. 4517-4522); invertase, which is a periplasm-localized protein (no GPI anchor is used); and the like.

First, (a) use of GPI anchor is described. The gene coding for a protein localized on a cell surface by a GPI anchor has, in order from the N-terminal, a gene coding for a secretion signal sequence, a gene coding for a cell surface-localized protein (a sugar chain binding protein), and a gene coding for a GPI anchor attachment recognition signal sequence. A cell surface-localized protein (a sugar chain binding protein) expressed from this gene in a cell is directed outside the cell membrane by a secretion signal, and then a GPI anchor attachment recognition signal sequence binds to the GPI anchor of the cell membrane via a specifically truncated C-terminal portion to immobilize the protein on the cell membrane. Subsequently, the protein is cleaved near the root of the GPI anchor by PI-PLC, and integrated into the cell wall, and immobilized on the cell surface, resulting in display of the protein on the cell surface.

Here, the secretion signal sequence refers to an amino acid sequence rich in highly hydrophobic amino acids, that is linked to the N terminal of a protein that is generally secreted outside the cell, including the periplasm, i.e., secretory protein, and is usually eliminated when the secretory protein is secreted from inside the cell through the cell membrane to the outside the cell. Any secretion signal sequence may be used irrespective of its origin as long as the secretion signal sequence can direct the expression product to the cell membrane. For example, the secretion signal sequence of glucoamylase, the signal sequence of yeast α- or a-agglutinin, the secretion signal sequence of the expression product itself are suitably used for the secretion signal sequence. The secretion signal sequence and the pro-sequence may partially or entirely may remain in the N terminal without affecting the activity of a protein fused to cell surface binding proteins adversely.

Here, the GPI anchor refers to a glycolipid having a basic structure of ethanolamine-phosphate-6-mannose-α1-2-mannose-α1-6-mannose-α1-4-glucosamine-α1-6-inositol-phospholipid called glycosyl phosphatidylinositol (GPI), and PI-PLC refers to phosphatidylinositol-dependent phospholipase C.

The GPI anchor attachment recognition signal sequence is a sequence recognized upon the binding of the GPI anchor to a cell surface-localized protein and is usually located at or near the C-terminal of the cell surface-localized protein. For example, the sequence of the C-terminal portion of yeast α-agglutinin is suitably used for the GPI anchor attachment signal sequence. Since a GPI anchor attachment recognition signal sequence is contained in the C-terminal of the sequence of 320 amino acids from the C-terminal of α-agglutinin, a DNA sequence coding for the sequence of 320 amino acids from the C-terminal is particularly useful as a gene for use in the method.

Therefore, for example, in a sequence having a DNA coding for a secretion signal sequence-a structural gene coding for a cell surface-localized protein-a DNA sequence coding for a GPI anchor attachment recognition signal, the entire or a part of the sequence of the structural gene coding for a cell surface-localized protein can be replaced with a DNA sequence coding for the enzyme of interest so as to obtain a recombinant DNA for displaying the enzyme of interest on the cell surface via a GPI anchor. In case of the cell surface-localized protein is α-agglutinin, it is preferable to introduce a DNA coding for the enzyme of interest such that the sequence coding for the sequence of 320 amino acids from the C-terminal of the α-agglutinin is retained. For this purpose, the "3' half region of α-agglutinin gene" may be used. Such a recombinant DNA can be introduced into a yeast for expression to display the enzyme on the cell surface, where the enzyme is immobilized on the surface via the C-terminal.

Next, (b) use of a sugar chain binding domain is described. The cell surface-localized protein can be a sugar chain binding protein, and the sugar chain binding domain thereof has a plurality of sugar chains which can interact or be entangled with sugar chains present in the cell wall to leave the protein on the cell surface. Examples include sugar chain binding sites of lectin, lectin-like proteins, and the like. Typical examples include the flocculation functional domain of a GPI anchor protein and the flocculation functional domain of a FLO protein. The flocculation functional domain of a GPI anchor protein refers to a domain that is located on the side of N-terminal relative to the GPI anchoring domain, has a plurality of sugar chains, and is thought to be involved in flocculation.

The linkage of sugar chain binding domain (flocculation functional domain) of a cell-surface localized protein with the enzyme of interest allows the enzyme to be displayed on the cell surface. Depending on the enzyme of interest, the enzyme may be liked (1) on the side of N-terminal or (2) on the side of C-terminal of the sugar chain binding domain (flocculation functional domain) of a cell surface-localized protein, or the same or different enzymes may be liked (3) on both sides of N-terminal and C-terminal. For example, (1) a DNA coding for a secretion signal sequence-a gene coding for the enzyme of interest-a structural gene coding for the sugar chain binding domain (flocculation functional domain) of a cell surface-localized protein or (2) a DNA coding for a secretion signal sequence-a structural gene coding for the sugar chain binding domain (flocculation functional domain) of a cell surface-localized protein-a gene coding for the enzyme of interest may be produced to obtain a recombinant DNA for displaying the enzyme of interest on the cell surface. Using the flocculation functional domain, the DNA sequence coding for a GPI anchor attachment recognition signal sequence may be partially present or may not be present in the recombinant DNA since the GPI anchor is not involved in cell surface display. The use of the flocculation functional domain is very advantageous in that: the enzyme can be displayed on the cell surface in a more suitable length because the length of the domain can be easily modified (for example, any of Floshort and Flolong can be selected); and the enzyme can be linked on either side of the N-terminal or the C-terminal.

Next, (c) use of a periplasm protein (another receptor molecule or target receptor molecule) is described. This method is based on the fact that the enzyme of interest can be expressed on the cell surface as a fused protein with the periplasm protein. An example of the periplasm protein may be invertase (Suc2 protein). The enzyme of interest may be suitably fused on the side of N-terminal or C-terminal depending on the periplasm protein.

The element (also referred to as "cell surface display factor") for use in any of the surface display techniques of the foregoing (a) to (c) may also be contained in the gene expression cassette for the enzyme by following the description given above. More specifically, the cell surface display factor may be ligated to the gene for enzyme to be expressed, at a desired arrangement together with a secretion signal sequence depending on the cell surface display factor used, and the ligation is arranged between a promoter and a terminator. The cell surface display factor may be obtained from microorganisms that express it by PCR or hybridization with primers or a probe designed based on known sequence information. Also, the surface display factors may be conveniently excised in a suitable form for vector preparation from a known plasmid (for example, *Appl. Environ. Microbiol.*, 2004, Vol. 70, pp. 1207-1212) containing, together with the genes of the cell surface display factors, the gene for enzyme to be expressed (for example, endoglucanase, cellobiohydrolase, or β-glucosidase), a secretory signal, and expression regulatory sequences such as a promoter and a terminator so as to prepare an insert.

A method for secretory expression of an enzyme outside a yeast cell is well known to those skilled in the art. A recombinant DNA in which the structural gene of the enzyme of interest is linked to a DNA coding for the secretion signal sequence may be prepared and introduced into a yeast.

Naturally, a method for expression of a gene in a yeast cell is also well known to those skilled in the art. In this case, a recombinant gene to which the structural gene of interest is linked without using the cell surface display factor such as the sugar chain binding domain (flocculation functional domain) of the cell surface-localized protein or the secretion signal as described above may be prepared and introduced into a yeast.

The synthesis and the linkage of DNA including various sequences may be performed using techniques commonly used by those skilled in the art. For example, the linkage of the secretion signal sequence and the structural gene for the enzyme of interest can be carried out using site-directed mutagenesis technique, thereby allowing accurate cleavage of secretion signal sequence and active expression of enzyme.

A vector can be constructed for the integration of a cellulose-degrading enzyme with a yeast δ sequence. The vector for use in the present invention can contain a pair of δ sequences (which allow homologous recombination with δ sequences present in large numbers on a yeast chromosome) and an enzyme gene.

The gene for enzyme to be expressed may usually be designed to be in a vector in the form of the expression cassette as mentioned above. That is, the enzyme gene may be contained in a vector together with expression regulatory factors such as a promoter, a terminator, and the like. The expression cassette may be designed such that the enzyme to be expressed is displayed on the cell surface as described above.

In the vector for use in the present invention, the enzyme expression cassette may be arranged between a pair of δ sequences so as to attain homologous recombination with δ sequences present in large numbers on a yeast chromosome. The vector may also be conveniently referred to as the "δ integration vector". Preferably, the vector may be in the form of a plasmid. It is preferable that the vector is a yeast-*E. coli* shuttle vector for facilitating the procedure for obtaining a DNA. The vector may contain regulatory sequences as described above as necessary. Such a vector has an origin of replication (Ori) of 2 μm plasmid for yeast and an origin of replication of ColE1 as well as a yeast selectable marker (described below) and an *E. coli* selectable marker (such as a drug-resistant gene).

Any known marker may be used for the yeast selectable marker. Examples include drug-resistant genes and auxotrophic marker genes (such as genes coding for imidazoleglycerol phosphate dehydratase (HIS3), beta-isopropylmalate dehydrogenase (LEU2), tryptophan synthase (TRP5), arginosuccinase lyase (ARG4), N-(5'-phosphoribosyl)anthranilate isomerase (TRP1), histidinol dehydrogenase (HIS4), orotidine-5-phosphate decarboxylase (URA3), dihydroorotic acid dehydrogenase (URA1), galactokinase (GAL1), alpha-aminoadipate reductase (LYS2), and the like). For example, auxotrophic marker genes (for example, HIS3, LEU2, URA3, TRP1 defective markers) may be preferably used. A yeast selectable marker may be arranged together with the enzyme expression cassette between a pair of δ sequences. The arrangement (upstream or downstream) and the direction (forward or reverse) of the yeast selectable marker relative to the enzyme expression cassette are not limited.

For the expression of the genes for a plurality of cellulose-degrading enzymes, δ integration vectors each containing the gene for the enzyme may be constructed as vectors for the expression of the respective enzymes. For example, for the expression of the genes for three types of cellulases, endoglucanase, cellobiohydrolase, and β-glucosidase, three δ integration vectors containing the genes of the respective enzymes may be constructed. Preferably, the δ integration vectors containing the genes of the respective enzymes are designed to have an identical yeast selectable marker.

It may be sufficient that a vector eventually prepared has such a configuration that it contains the desired elements (containing, for example, δ sequences, an enzyme gene and an expression regulatory sequence thereof, and a yeast selectable marker are contained; and preferably, further containing, depending on the manner of enzyme gene expression, additional elements such as a secretion signal sequence and a cell surface display factor (depending on the factor used, the factor may be located on the 3' side or 5' side relative to the enzyme gene to be expressed)). The preparation procedure may depend on the materials used (for example, a backbone vector, inserts of elements such as an enzyme gene or a cell surface display factor, which may be excised from a known vector).

A plurality of δ integration vectors designed for the expression of the genes of a plurality of cellulose-degrading enzymes may be co-introduced into a yeast host. The "introduction" of a vector into a yeast host means not only the introduction of a gene or DNA present in the vector into the yeast host cell but also the expression thereof by the yeast host. It may also be called transformation, transduction, transfection, or gene recombination. Examples of the gene or DNA introduction include the lithium acetate method, the protoplast method, the electroporation method, and the like. For introduction into yeast cell, specific examples include the lithium acetate method, the protoplast method, and the like. The DNA to be introduced may undergo homologous recombination with δ sequences of the yeast host and may be incorporated into the chromosome thereof. The terms "co-introduction" and "co-transformation" mean that the plurality of vectors may be introduced simultaneously or sequentially, and when vectors are introduced sequentially, the order of introduction is not limited.

The kind of a yeast that serves as a host is not particularly limited and, in particular, yeasts that belong to the genus *Saccharomyces* are preferable, and *Saccharomyces cerevisiae* is preferable. A yeast host may be genetically modified such that the ability for alcohol fermentation from monosaccharide (for example, glucose), which is the substrate for fermentation obtained by cellulose degradation, can be enhanced.

The co-introduction into a yeast host of δ integration vectors for the expression of the genes of a plurality of cellulose-degrading enzymes may be performed repetitively. Preferably, the plurality of integration vectors may be designed to have an identical yeast selectable marker in a first co-introduction, and also in repeating co-introduction. The δ integration with a plurality of δ integration vectors that have an identical yeast selectable marker is also referred to as "cocktail δ integration." More preferably, in repetitive co-introduction, a different yeast selectable marker from the yeast selectable marker used in the first or previous co-introduction may be used.

Subsequent to the foregoing co-introduction, a transformed yeast to which a desired cellulose degradation ability has been imparted may be selected by means of a screening for the cellulose degradation ability. For this purpose, the phosphoric acid-swollen cellulose (PASC) degradation activity may be used (the procedure of which is illustrated in Example 3 below). For example, a screening by measuring for the PASC degradation activity may be used subsequent to a screening by means of a yeast selectable marker. If it is planed that the enzyme is displayed on the surface, it is also possible to use a screening for colony formation on a medium for which PASC is used as a sole carbon source.

For improving the PASC degradation activity of the transformed yeast, important is the balance of expression of three types of cellulases, endoglucanase, cellobiohydrolase, and β-glucosidase. Therefore, the ratio of endoglucanase to β-glucosidase (endoglucanase gene/β-glucosidase gene) for cellulase genes introduced into yeast may be 2 or greater, preferably 3 or greater, more preferably 4 or greater, and still more preferably 5 or greater. The ratio of endoglucanase to cellobiohydrolase (endoglucanase gene/cellobiohydrolase gene) for cellulase genes introduced into yeast may be 1 or greater and preferably 2 or greater.

Also encompassed within the scope of the present invention is a yeast obtained by the co-introduction of δ integration vectors for the expression of the genes for a plurality of cellulose-degrading enzymes as described above, which can suitably expresses the plurality of co-introduced cellulose-degrading enzymes and hydrolyze cellulose, also referred to as a "cellulose degradable yeast". Such a yeast may be used also in the hydrolysis of cellulose-containing materials (for example, bagasse, rice straw, and the like).

The present invention shall be described below by way of examples, but the present invention is not limited by the examples.

EXAMPLES

The strains used in the examples, *Saccharomyces cerevisiae* BY4741 (*Yeast*, 1998, Vol. 14, pp. 115-132) and *Saccharomyces cerevisiae* MT8-1 (MATa ade his3 leu2 trp1 ura3 strain) (*Yeast*, 1985, Vol. 1, pp. 67-77), were obtained from Funakoshi Corporation and the author of *Yeast*, 1985, Vol. 1, pp. 67-77, respectively.

All of the PCR amplifications mentioned in the examples were performed using a KOD-Plus-DNA polymerase (Toyobo Co., Ltd.).

All of the yeast transformations mentioned in the examples were performed according to the lithium acetate method using Yeastmaker yeast transformation system (Clontech Laboratories, Palo Alto, Calif., USA).

Preparation Example 1

Construction of pIHPGBGL, pIHPGAGCBHII, and pIWPGAGEGII, and pIWPGAGEGPGBGL

The plasmids pIHPGAGCBHII and pIWPGAGEGPGBGL were constructed, which were for expression by ordinary integration of cellobiohydrolase II from *Trichoderma reesei*, and of endoglucanase II from *Trichoderma reesei* and β-glucosidase 1 from *Aspergillus aculeatus*, respectively. The procedure of the construction of these plasmids is described below.

The promoter sequence (pPGK) and terminator sequence (tPGK) of PGK1, which is one of the phosphoglycerate kinases present on a yeast genome, were amplified by PCR using primers pPGKF (XhoI) (SEQ ID NO. 1) and pPGKR (SmaI) (SEQ ID NO. 2), and tPGKF (SmaI) (SEQ ID NO. 3) and tPGKR (NotI) (SEQ ID NO. 4), respectively, with the genomic DNA of a yeast *Saccharomyces cerevisiae* BY4741 was used as a template.

The amplified pPGK and tPGK were inserted into the XhoI/SmaI site and SmaI/NotI site of a vector plasmid pBluescript II KS+ (Stratagene Corporation), respectively.

A sequence containing pPGK and tPGK was obtained from the constructed plasmid by BSSHII restriction enzyme digestion and inserted into the BSSHII site of yeast expression vectors pRS403 (HIS3 yeast expression vector: Stratagene Corporation) and pRS404 (TRP1 yeast expression vector: Stratagene Corporation), and the obtained respective plasmids were named pIHPG and pIWPG, respectively.

The genes for BGL/AG-anchor, CBHII/AG-anchor, and EGII/AG-anchor were amplified by PCR using primers BGLF (XbaI) (SEQ ID NO. 5) and BGLR (XbaI) (SEQ ID NO. 6), CBHIIF (XbaI) (SEQ ID NO. 7) and CBHIIR (XbaI) (SEQ ID NO. 8), and EGIIF (NheI) (SEQ ID NO. 9) and EGIIR (SmaI) (SEQ ID NO. 10), respectively, with pBG211 (a vector for β-glucosidase surface expression having AG-anchor: the 3' half region of α-agglutinin gene (a region of nucleotides from position 991 to 1953 of the α-agglutinin gene coding region and a 445 bp terminator region downstream of the coding region): *Appl. Environ. Microbiol.*, 2004, Vol. 70, pp. 1207-1212), pFCBH2w3 (a vector for cellobiohydrolase II surface expression having the 3' half region of α-agglutinin gene: *Appl. Environ. Microbiol.*, 2004, Vol. 70, pp. 1207-1212), and pEG23u31H6 (a vector for endoglucanase II surface expression having the 3' half region of α-agglutinin gene: *Appl. Environ. Microbiol.*, 2004, Vol. 70, pp. 1207-1212), respectively, as templates.

The amplified BGL/AG-anchor and CBHII/AG-anchor were inserted into pIHPGs, the obtained respective plasmids were respectively named pIHPGBGL and pIHPGAGCBHII, and the amplified EGII/AG-anchor gene was inserted into pIWPG and the obtained plasmid was named pIWPGAGEGII.

The pPGK-BGL/AG-anchor gene was amplified by PCR using primers pPGKF (NotI) (SEQ ID NO. 11) and tAGR (NotI) (SEQ ID NO. 12) with pIHPGBGL as a template, and inserted into the NotI site of pIWPGAGEGII, and the obtained plasmid was named pIWPGAGEGPGBGL.

Preparation Example 2

Construction of pIU-PGAGEGII and pIW-PGAGCBHII

The plasmids pIU-PGAGEGII and pIW-PGAGCBHII were constructed, which were for expression by ordinary integration of endoglucanase II from *Trichoderma reesei* and of cellobiohydrolase II from *Trichoderma reesei*, respectively. The procedure of the construction of these plasmids is described below.

A region containing the promoter sequence (pPGK) of PGK1, endoglucanase II gene, and AG-anchor in this order was amplified by PCR using primers pPGKF (NotI) (SEQ ID NO. 11) and tAGR (NotI) (SEQ ID NO. 12) with a plasmid pIWAGEGII (*Biotechnol. J.*, 2010, Vol. 5, pp. 449-455) as a template.

The amplified insert DNA was inserted into the NotI site of a vector plasmid pRS406 (URA3 yeast expression vector: Stratagene Corporation) and the obtained plasmid was named pIU-PGAGEGII.

A region containing the promoter sequence (pPGK) of PGK1, cellobiohydrolase II gene, and AG-anchor in this order was amplified by PCR using primers pPGKF (NotI) and tAGR (NotI) with a plasmid pIHAGCBHII (*Biotechnol. J.*, 2010, Vol. 5, pp. 449-455) as a template.

The amplified insert DNA was inserted into the NotI site of a vector plasmid pRS404 (TRP1 yeast expression vector: Stratagene Corporation) and the obtained plasmid was named pIW-PGAGCBHII.

Preparation Example 3

Construction of pδW and pδU

The plasmids pδW and pδU, which were vectors for δ integration, were constructed as described below.

First, the 5' 167 bp of a δ sequence (5' δ sequence) present on a yeast genome was amplified by PCR using primers 5' DSF (SacI) (SEQ ID NO. 13) and 5' DSR (SacI) (SEQ ID NO. 14) with the genomic DNA of *Saccharomyces cerevisiae* BY4741 as a template.

Next, the amplified insert DNA (5' δ sequence) was inserted into the SacI site of a vector plasmid pBluescript II KS+.

Similarly, the 3' 167 bp of the δ sequence (3' δ sequence) was amplified by PCR using primers 3' DSF (KpnI) (SEQ ID NO. 15) and 3' DSR (KpnI) (SEQ ID NO. 16), and inserted into the kpnI site of pBluescript II KS+ into which the foregoing 5' δ sequence had been introduced.

A TRP1 defective marker (TRP1d) was amplified by PCR using primers TRP1dF (XhoI) (SEQ ID NO. 17) and TRP1dR (XhoI) (SEQ ID NO. 18) from TRP1 gene present on a plasmid pRS404 (TRP1 yeast expression vector: Stratagene Corporation), and inserted into the XhoI site of pBluescript II KS+ into which the foregoing 5' δ sequence and 3' δ sequence had been introduced, and the obtained plasmid was named pδW. Thus, pδW is a plasmid, which is a vector for δ integration, containing the TRP 1 defective marker as a selectable marker and a yeast δ sequence.

Similarly, a URA3 defective marker (URA3d) was amplified by PCR using primers URA3dF (XhoI) (SEQ ID NO. 19) and URA3dR (XhoI) (SEQ ID NO. 20) from URA3 gene present on a plasmid pRS406 (URA3 yeast expression vector: Stratagene Corporation), and inserted into the XhoI site of a vector plasmid pBluescript II KS+ into which the foregoing 5' δ sequence and 3' δ sequence had been introduced, and the obtained plasmid was named pδU. Thus, pδU is a plasmid, which is a vector for δ integration, containing the URA3 defective marker as a selectable marker and a yeast δ sequence.

Preparation Example 4

Construction of pδH

The plasmid pδH, which was a vector for δ integration, was constructed as described below.

A HIS3 defective marker (HIS3d) was amplified by PCR using primers HIS3dF (XhoI) (SEQ ID NO. 21) and HIS3dR (XhoI) (SEQ ID NO. 22) from HIS3 gene present on a plasmid pRS403 (HIS3 yeast expression vector: Stratagene Corporation) and introduced into the XhoI site of pδseq (*Appl. Microbiol. Biotechnol.*, 2010, Vol. 85, pp. 1491-1498), and the obtained plasmid was named pδH. Thus, pδH is a plasmid, which is a vector for δ integration, containing the HIS3 defective marker as a selectable marker and a yeast δ sequence.

Example 1

Construction of pδW(U, H)-PGAGBGL, pδW(U, H)-PGAGCBHII, and pδW(U, H)-PGAGEGII

Into the vectors for δ integration, plasmids pδW, pδU, and pδH, each of the expression cassettes for the respective cellulases, i.e., cellulose-degrading enzymes, to which are also hereinafter simply referred as "cellulase expression cassette(s)", was inserted to construct nine types of cellulase expression δ integration vectors, plasmids pδW-PGAGBGL, pδW-PGAGCBHII, and pδW-PGAGEGII, pδU-PGAGBGL, pδU-PGAGCBHII, and pδU-PGAGEGII, and pδH-PGAGBGL, pδH-PGAGCBHII, and pδH-PGAGEGII. The procedure of construction of these plasmids is described below.

A PCR was performed using primers pPGKF (NotI) (SEQ ID NO. 11) and tAGR (NotI) (SEQ ID NO. 12) with the plasmids pIHPGBGL, pIHPGAGCBHII, and pIWP-GAGEGII prepared in Preparation Example 1 as templates to amplify respective cellulase expression cassettes (regions which contain a promoter, a secretory signal, an expression enzyme gene, and a cell surface display factor in this order, that is, PGK promoter, secretion signal, β-glucosidase gene, and AG-anchor; PGK promoter, secretion signal, cellobiohydrolase II gene, and AG-anchor; and PGK promoter, secretion signal, endoglucanase II gene, and AG-anchor, respectively, in the described order).

The aforementioned respective cellulase expression cassettes were inserted into the NotI site of pδW or pδU produced in Preparation Example 3, and the obtained plasmids were respectively named pδW-PGAGBGL, pδW-PGAGCBHII, and pδW-PGAGEGII, and pδU-PGAGBGL, pδU-PGAGCBHII, and pδU-PGAGEGII.

A plasmid pIHAGBGL-NotI (*Biotechnol. J.*, 2010, Vol. 5, pp. 449-455) and the plasmids pIU-PGAGEGII and pIW-PGAGCBHII produced in Preparation Example 2 were digested with NotI to obtain the respective cellulase expression cassettes (regions which contain a promoter, a secretory signal, an expression enzyme gene, and a cell surface display factor in this order, that is, PGK promoter, secretion signal, β-glucosidase gene, and AG-anchor; PGK promoter, secretion signal, cellobiohydrolase II gene, and AG-anchor; and PGK promoter, secretion signal, endoglucanase II gene, and AG-anchor, respectively, in the described order).

The aforementioned respective cellulase expression cassettes were inserted into the NotI site of pδH produced in Preparation Example 4, and the obtained plasmids were respectively named pδH-PGAGBGL, pδH-PGAGCBHII, and pδH-PGAGEGII.

Figure 2:
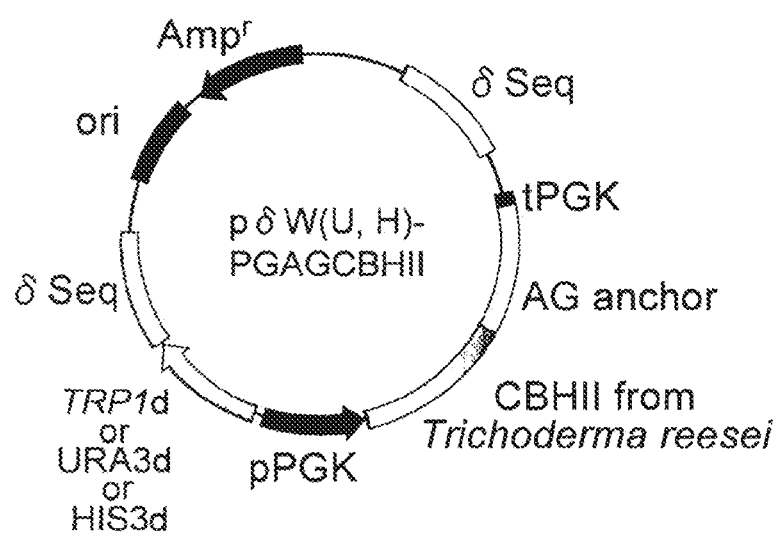
FIG. 2 is a schematic drawing showing the vector configuration of pδW-PGAGCBHII, pδU-PGAGCBHII, and pδH-PGAGCBHII.
Figure 3:
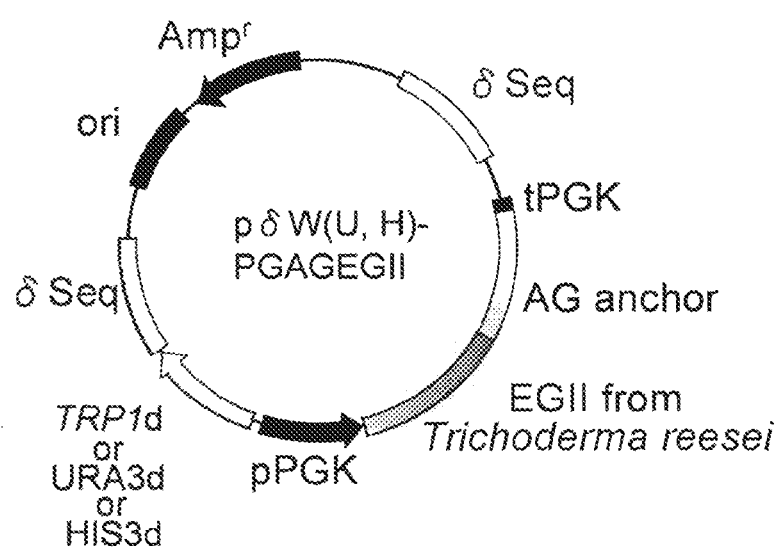
FIG. 3 is a schematic drawing showing the vector configuration of pδW-PGAGEGII, pδU-PGAGEGII, and pδH-PGAGEGII.

Schematic drawings of each of these plasmids are presented in FIGS. 1 to 3 (FIG. 1: pδW-PGAGBGL, pδU-PGAGBGL, and pδH-PGAGBGL, FIG. 2: pδW-PGAGCBHII, pδU-PGAGCBHII, and pδH-PGAGCBHII, and FIG. 3: pδW-PGAGEGII, pδU-PGAGEGII, and pδH-PGAGEGII).

Example 2

Generation of Transformed Yeast (1)

Among the plasmids prepared in Example 1, three plasmids having the TRP1 defective marker, pδW-PGAGBGL, pδW-PGAGEGII, and pδW-PGAGCBHII, were simultaneously subject to a yeast *Saccharomyces cerevisiae* MT8-1 strain (MATa ade his3 leu2 trp1 ura3 strain), and co-transformed by the lithium acetate method (1-cycle cocktail δ integration). To screen for successful transformation, screening by visual observation for colony formation on a selective medium plate free of tryptophan and containing PASC as a sole carbon source, and then screening by measuring for the PASC degradation activity (the procedure is as presented in Examples 3 below) were performed to obtain a transformant MT8-1/cocδBEC strain by 1-cycle cocktail δ integration.

Moreover, the MT8-1/cocδBEC strain was co-transformed in the same manner with three plasmids having the URA3 deficient marker, pδU-PGAGBGL, pδU-PGAGEGII, and pδU-PGAGCBHII (2-cycle cocktail δ integration). Screening for successful transformation was performed in the same manner as in the screening to obtain the MT8-1/cocδBEC strain except that the selective medium was free of uracil instead of tryptophan. As a result, a transformant MT8-1/cocδBECII strain by 2-cycle cocktail δ integration was obtained.

As a control, a yeast *Saccharomyces cerevisiae* MT8-1 strain was transformed with pIHPGAGCBHII and pIWP-GAGEGPGBGL produced in Preparation Example 1 (referred to as "ordinary integration" for convenience) to obtain a transformant MT8-1/IBEC strain. On the transformant by ordinary integration, screening by visual observation for colony formation on a selective medium plate free of histidine and tryptophan and containing glucose as a sole carbon source, and then screening by measuring for the PASC degradation activity were performed.

Example 3

Measurement for Activity of Transformant (1)

The transformant MT8-1/cocδBEC strain and MT8-1/cocδBECII strain by cocktail δ integration and the transformant MT8-1/IBEC strain by ordinary integration, generated in Example 2, were measured for the β-glucosidase activity and the PASC degradation activity. The procedures of measuring for the respective activities are as presented below.

<β-Glucosidase Activity Measurement>

The measurement for the β-glucosidase activity of the yeast cells was performed as follows:

(1) Inoculate yeast cells into 5 ml of YPD medium (glucose-peptone-yeast extract medium) and culture for 24 hours;

(2) Wash yeast cells twice with distilled water;

(3) Prepare 500 μl of reaction solution (composition: 100 μl of 10 mM pNPG (p-nitrophenyl-β-D-glucopyranoside) (final concentration of 2 mM); 25 μl of 1M NaAc (pH 5.0) (final concentration of 50 mM); 100 μl of yeast cells; and 275 μl of distilled water) and react at 30° C. for 10 minutes;

(4) After reaction, add 500 μl of 3M $Na_2CO_3$ to terminate reaction; and (5) Centrifuge at 10000 g for 5 minutes and then measure absorbance at 400 nm $ABS_{400}$ of supernatant.

<PASC Degradation Activity Measurement>

Measurement for the PASC degradation activity of the yeast cells was performed as follows:

(1) Inoculate yeast cells into 5 ml of YPD media and culture for 72 hours;

(2) Wash yeast cells twice with distilled water;

(3) Prepare 500 μl of reaction solution (composition: 250 μl of PASC; 25 μl of 1M NaAc (pH 5.0) (final concentration of 50 mM); 100 μl of yeast cells (final concentration of 10 g (wet weight)/l); and 125 μl of distilled water) and react at 50° C. for 4 hours;

(4) Centrifuge reacted sample, add 100 μl of Somogyi copper reagent (Sigma-Aldrich) to 100 μl of supernatant, incubate at 100° C. for 20 minutes, and immediately cool on ice;

(5) After cooling, mix 200 μl of Nelson reagent (Sigma-Aldrich) to dissolve reduced copper precipitate to produce color;

(6) Leave to stand still for 30 minutes and centrifuge at 20° C. at 14000 rpm for 10 minutes, mix 800 μl of distilled water with 200 μl of supernatant, and measure absorbance at 520 nm. The amount of enzyme that releases 1 mmol of reducing sugar in terms of glucose in 1 minute is 1 U.

Figure 4:
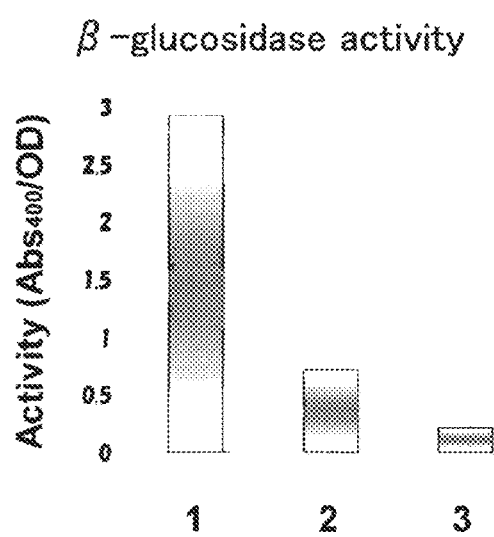
FIG. 4 is a bar chart showing the β-glucosidase activity of each of an MT8-1/cocδBEC strain, an MT8-1/cocδBECII strain, and an MT8-1/IBEC strain.
Figure 5:
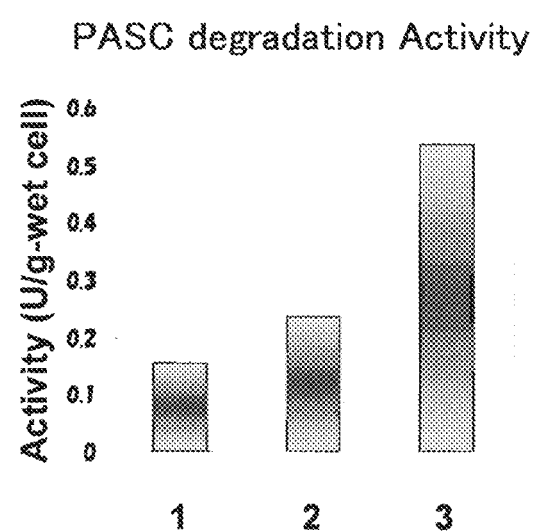
FIG. 5 is a bar chart showing the PASC (phosphoric acid-swollen cellulose) degradation activity of each of an MT8-1/cocδBEC strain, an MT8-1/cocδBECII strain, and an MT8-1/IBEC strain.

FIGS. 4 and 5 show the β-glucosidase activity and the PASC (phosphoric acid-swollen cellulose) degradation activity, respectively, of the MT8-1/cocδBEC strain, the MT8-1/cocδBECII strain, and the MT8-1/IBEC strain. In FIG. 4, the vertical axis is for post-reaction absorbance at 400 nm, which is an indicator of the β-glucosidase enzyme activity. In FIG. 5, the vertical axis is for the enzyme amount Upper gram of wet weight of yeast, which is an indicator of the PASC degradation activity. In both FIGS. 4 and 5, "1" on the horizontal axis is for the MT8-1/IBEC strain, "2" is for the MT8-1/cocδBEC strain, and "3" is for the MT8-1/cocδBECII strain.

It was found that the transformant MT8-1/cocδBEC strain by 1-cycle cocktail δ integration had a lower β-glucosidase activity but a greater PASC degradation activity than the transformant MT8-1/IBEC strain by ordinary integration. It was observed that the transformant MT8-1/cocδBECII strain by 2-cycle cocktail δ integration had a further reduced β-glucosidase activity but a further increased PASC degradation activity.

Example 4

Confirmation for Gene Introduction of Transformant

The introduction of three genes, genes for β-glucosidase, cellobiohydrolase II, and endoglucanase II, into the transformant MT8-1/cocδBEC strain by cocktail δ integration and the transformant MT8-1/IBEC strain by ordinary integration, generated in Example 2, was investigated by colony PCR.

A yeast colony on selective medium plate was suspended in 20 μL of 0.25% (w/v) SDS and vortexed for 5 minutes. Next, 180 μL of distilled water was added, centrifugation was performed at 14000 rpm for 30 seconds, and the supernatant was collected. A PCR was performed using a KOD-plus-DNA polymerase with supernatant as a template. Primers used were BGL500-1000(F) (SEQ ID NO. 23) and BGL500-1000 (R) (SEQ ID NO. 24) for BGL, EGII300-800(F) (SEQ ID NO. 25) and EGII300-800(R) (SEQ ID NO. 26) for EGII, and CBHII300-800(F), (SEQ ID NO. 27) and CBHII300-800(R) (SEQ ID NO. 28) for CBHII.

Figure 6:
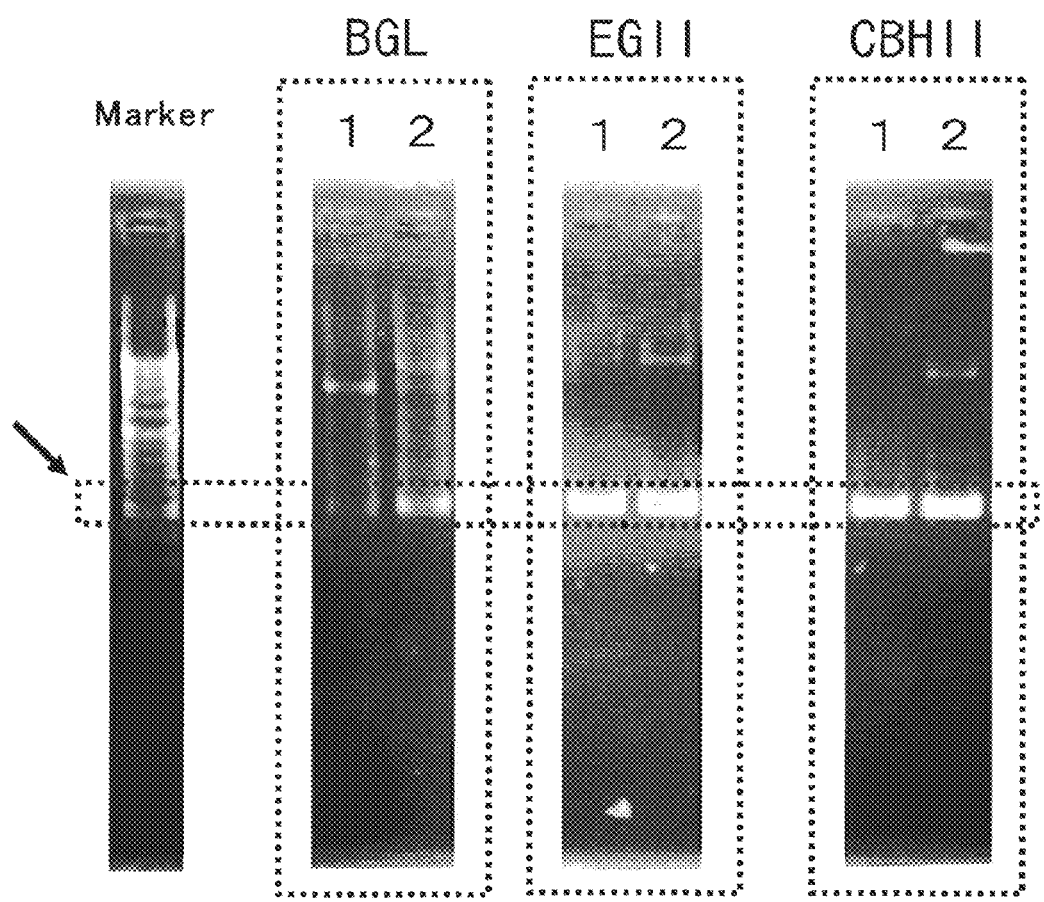
FIG. 6 is an electrophoretogram showing the results of colony PCR to determine the introduction of a β-glucosidase gene, a cellobiohydrolase II gene, and an endoglucanase II gene into an MT8-1/cocδBEC strain and an MT8-1/IBEC strain.

The results are shown in FIG. 6. The lanes for BGL show the results of β-glucosidase gene introduction, the lanes for EGII show the results of endoglucanase II gene introduction, and the lanes for CBHII show the results of cellobiohydrolase II gene introduction, in which lane 1 and lane 2 show the results of the transformant by ordinary integration and of the transformant by cocktail δ integration, respectively. It was confirmed that all of β-glucosidase gene, endoglucanase II gene, and cellobiohydrolase II gene were introduced into the transformant MT8-1/cocδBEC strain by cocktail δ integration.

Example 5

Generation of Transformed Yeast (2)

Among the plasmids prepared in Example 1, plasmids pδH-PGAGBGL having the HIS3 defective marker, pδU-PGAGEGII having the URA3 defective marker, and pδW-PGAGCBHII having the TRP1 defective marker were simultaneously subject to a yeast *Saccharomyces cerevisiae* MT8-1 strain (MATa ade his3 leu2 trp1 ura3 strain), and co-transformed by the lithium acetate method (ordinary δ integration). To screen for successful transformation, screening by visual observation for colony formation on a selective medium plate free of histidine, uracil and tryptophan and containing PASC as a sole carbon source, and then screening by measuring for the PASC degradation activity were performed to obtain a transformant MT8-1/cocδBEC strain by ordinary δ integration.

Among the plasmids prepared in Example 1, three plasmids having the TRP1 defective marker, pδW-PGAGBGL, pδW-PGAGEGII, and pδW-PGAGCBHII, were simultaneously subject to a yeast *Saccharomyces cerevisiae* MT8-1 strain (MATa ade his3 leu2 trp1 ura3 strain), and co-transformed by the lithium acetate method (1-cycle cocktail δ integration). To screen for successful transformation, screening by visual observation for colony formation on a selective medium plate free of tryptophan and containing PASC as a sole carbon source, and then screening by measuring for the PASC degradation activity were performed to obtain a transformant MT8-1/cocδBEC1 strain by 1-cycle cocktail δ integration.

Moreover, the MT8-1/cocδBEC1 strain was co-transformed in the same manner with three plasmids having the URA3 defective marker, pδU-PGAGBGL, pδU-PGAGEGII, and pδU-PGAGCBHII (2-cycle cocktail δ integration). Screening for successful transformation was performed in the same manner as in the screening to obtain an MT8-1/cocδ-BEC1 strain except that the selective medium was free of uracil instead of tryptophan. As a result, a transformant MT8-1/cocδBEC2 strain by 2-cycle cocktail δ integration was obtained.

Moreover, the MT8-1/cocδBEC2 strain was co-transformed in the same manner with three plasmids having the HIS3 defective marker, pδH-PGAGBGL, pδH-PGAGEGII, and pδH-PGAGCBHII (3-cycle cocktail δ integration). Screening for successful transformation was performed in the same manner as in the screening to obtain the MT8-1/cocδ-BEC1 strain except that the selective medium was free of histidine instead of tryptophan. As a result, a transformant MT8-1/cocδBEC3 strain by 3-cycle cocktail δ integration was obtained.

As a control, a yeast *Saccharomyces cerevisiae* MT8-1 strain was transformed with a plasmid pIHAGBGL-NotI (*Biotechnol. J.*, 2010, Vol. 5, pp. 449-455) and the plasmids pIU-PGAGEGII and pIW-PGAGCBHII, produced in Preparation Example 2, to obtain a transformant MT8-1/IBEC2 strain. On the transformant by ordinary integration, screening by visual observation for colony formation on a selective medium plate free of histidine, uracil and tryptophan and containing glucose as a sole carbon source, and screening by measuring for the PASC degradation activity were performed.

Example 6

Measurement for Activity of Transformant (2)

The transformant MT8-1/δBEC strain by ordinary δ integration, the transformants MT8-1/cocδBEC1 strain, MT8-1/cocδBEC2 strain, and MT8-1/cocδBEC3 strain by cocktail δ integration, and the transformant MT8-1/IBEC2 strain by ordinary integration generated in Example 5 and a wild strain were measured for the β-glucosidase activity and the PASC degradation activity, in the same manner as in Example 3.

Figure 7:
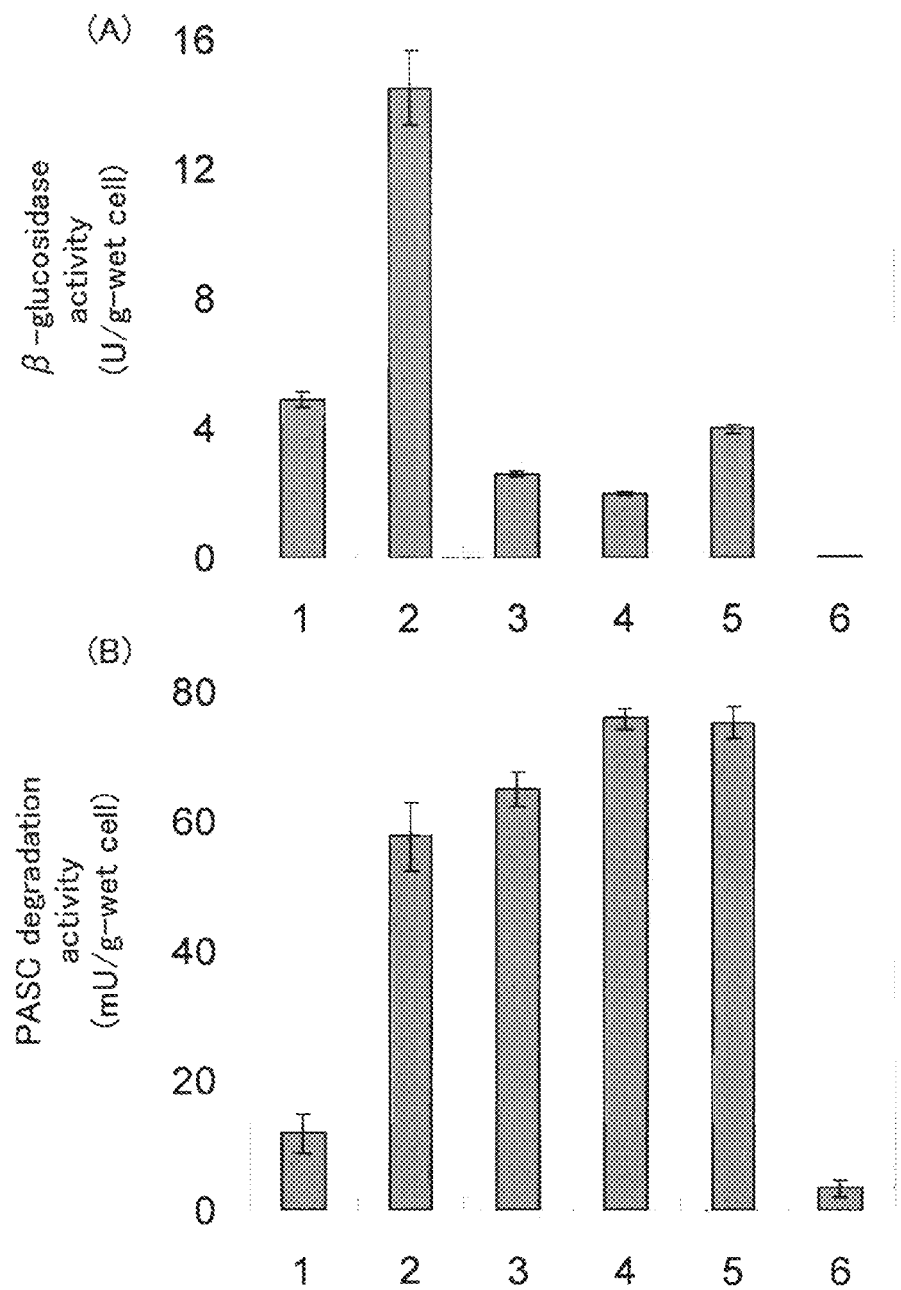
FIG. 7 provides bar charts showing the β-glucosidase activity (A) and the PASC degradation activity (B) of each of an MT8-1/δBEC strain, an MT8-1/cocδBEC1 strain, an MT8-1/cocδBEC2 strain, an MT8-1/cocδBEC3 strain, an MT8-1/IBEC2 strain, and a wild strain.

FIG. 7 provides bar charts showing the β-glucosidase activity (A) and the PASC degradation activity (B) of each of the MT8-1/δBEC strain, the MT8-1/cocδBEC1 strain, the MT8-1/cocδBEC2 strain, the MT8-1/cocδBEC3 strain, the MT8-1/IBEC2 strain, and the wild strain.

It was found that the β-glucosidase activity and the PASC degradation activity of the transformant MT8-1/δBEC strain by ordinary δ integration were both significantly higher than those of the transformant MT8-1/IBEC2 strain by ordinary integration. Also, it was found that the transformant MT8-1/cocδBEC1 strain by 1-cycle cocktail δ integration had a lower β-glucosidase activity but a greater PASC degradation activity than the transformant MT8-1/δBEC strain by ordinary δ integration. As seen in these results, while the β-glucosidase activity is in excess and the balance of expression of the three types of cellulases is inadequate in the transformant by ordinary δ integration, the balance of expression of the three types of cellulases is suitable to efficiently degrade PASC in the transformant MT8-1/cocδBEC1 strain by 1-cycle cocktail δ integration. The transformants MT8-1/cocδBEC2 strain and MT8-1/cocδBEC3 strain by 2-cycle and 3-cycle cocktail δ integration, respectively, have a further increased PASC degradation activity, making the balance of expression of the three cellulases more suitable.

Example 7

Determination of the Copy Number of Gene Introduced for Transformant

The copy number for each of three genes introduced, β-glucosidase gene, cellobiohydrolase II gene, and endoglucanase II gene, was determined by real-time PCR for the transformant MT8-1/δBEC strain by ordinary δ integration, the transformant MT8-1/cocδBEC1 strain, MT8-1/cocδBEC2 strain, and MT8-1/cocδBEC3 strain by cocktail δ integration, and the transformant MT8-1/IBEC2 strain by ordinary integration.

A genomic DNA was extracted with YeaStar Genomic DNA kit (Zymo Research Corporation) from 5 mL of yeast cells cultured on selective medium. A real-time PCR was performed with an ABI PRISM 7000 Sequence Detection System (Applied Biosystems) with this genomic DNA as a template. Primers used were BGL761F (SEQ ID NO. 29) and BGL858R (SEQ ID NO. 30) for BGL, EGII694F (SEQ ID NO. 31) and EGII774R (SEQ ID NO. 32) for EGII, and CBHII571F, (SEQ ID NO. 33) and CBHII653R (SEQ ID NO. 34) for CBHII. The results were determined by real-time PCR and standardized by using, as the control, PGK1 gene of housekeeping gene.

Figure 8:
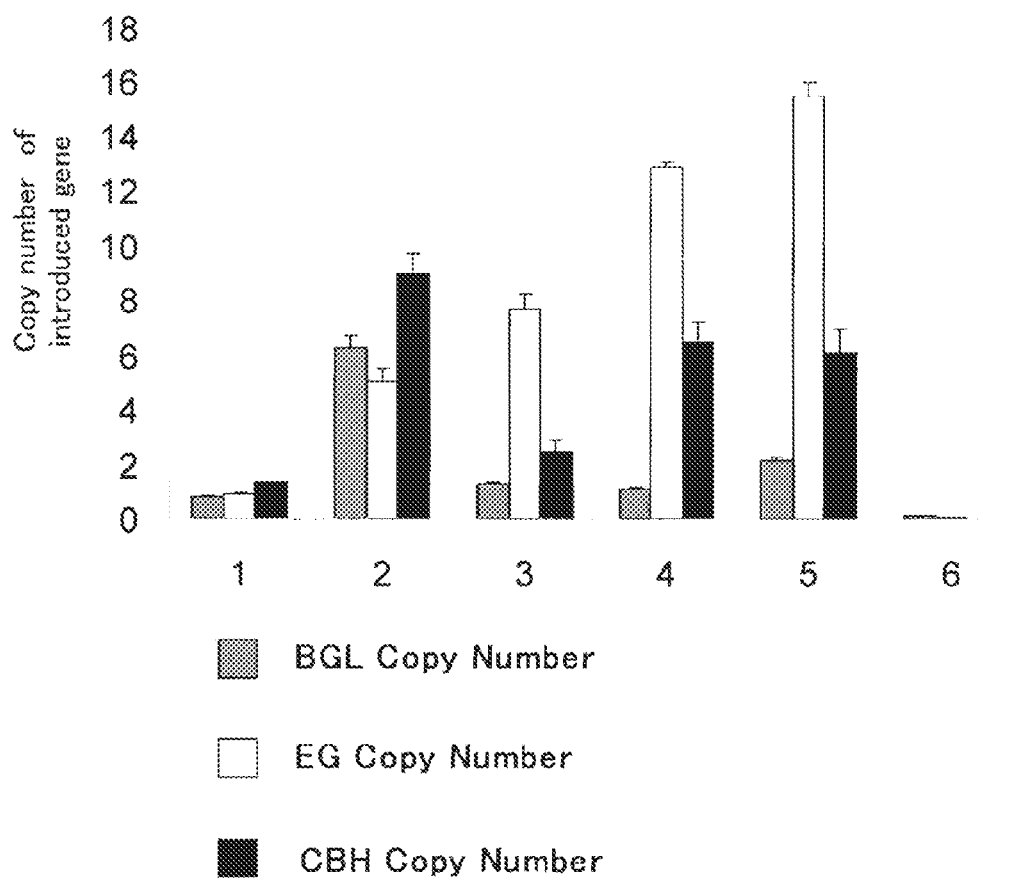
FIG. 8 is a bar chart showing the results of real-time PCR for measuring the number of copies of a β-glucosidase gene, a cellobiohydrolase II gene, and an endoglucanase II gene introduced into an MT8-1/δBEC strain, an MT8-1/cocδ-

FIG. 8 shows the results. It was found that while the copy numbers of β-glucosidase gene, endoglucanase II gene, and cellobiohydrolase II gene introduced were 6, 5, and 9, respectively, for the transformant MT8-1/δBEC strain by ordinary δ integration, which were nearly comparable to each other; the copy numbers of β-glucosidase gene, endoglucanase II gene, and cellobiohydrolase I gene introduced were 1, 8, and 2, respectively, for the transformant MT8-1/cocδBEC1 strain by 1-cycle cocktail δ integration, in which the copy number of endoglucanase II gene introduced was specifically elevated. Also, it was found that the copy number of endoglucanase II gene introduced was specifically elevated for the transformants MT8-1/cocδBEC2 strain and MT8-1/cocδBEC3 strain by 2-cycle and 3-cycle cocktail δ integration, respectively.

It was found that, as shown in FIGS. 7 and 8, in the production of cellulose degradable yeast by the introduction of genes for cellulases, the PASC degradation activity is increased as the ratio of the copy number of introduced gene for endoglucanase II to the copy number of introduced gene for each of other cellulases is increased. It was found that a yeast in which the ratio for genes of endoglucanase II to β-glucosidase (endoglucanase II gene/β-glucosidase gene) is 2 or greater and the ratio for genes of endoglucanase II to cellobiohydrolase II (endoglucanase II gene/cellobiohydrolase II gene) is 1 or greater has a much improved PASC degradation activity.

According to the present invention, a yeast having an improved cellulose degradation ability can be produced. Therefore, it is expected that bioethanol can be produced from lignocellulose-based biomass in a more cost effective way and that efficient and effective use of biomass toward post-petroleum society can be promoted.

The invention claimed is:

1. A method for producing a cellulose degradable yeast, comprising the step of: co-introducing genes coding for at least two cellulose-degrading enzymes into a yeast host via integration with a yeast δ sequence, wherein the at least two cellulose-degrading enzymes are a combination of enzymes comprising (A) endoglucanase and (B) β-glucosidase, and wherein the ratio for genes of (A)/(B) is 2 or greater.

2. The method according to claim 1, wherein the combination of enzymes is a combination of endoglucanase, cellobiohydrolase, and β-glucosidase.

3. The method according to claim 1, wherein the cellulose-degrading enzymes are designed to be displayed on a cell surface.

4. The method according to claim 1, wherein the step of co-introduction is repeated twice or more.

5. The method of claim 1, wherein the enzymes are a combination of enzymes consisting of (A) endoglucanase and (B) β-glucosidase.

6. A method for producing a cellulose degradable yeast, comprising the step of: co-introducing genes coding for at least two cellulose-degrading enzymes into a yeast host via integration with a yeast δ sequence, wherein the at least two cellulose-degrading enzymes are a combination of enzymes comprising (A) endoglucanase and (B) cellobiohydrolase, and wherein the ratio for genes of (A)/(B) is greater than 1.

7. The method according to claim 6, wherein the combination of enzymes is a combination of endoglucanase, cellobiohydrolase, and β-glucosidase.

8. The method according to claim 6, wherein the cellulose-degrading enzymes are designed to be displayed on a cell surface.

9. The method according to claim 6, wherein the step of co-introduction is repeated twice or more.

10. The method of claim 6, wherein the enzymes are a combination of enzymes consisting of (A) endoglucanase and (B) cellobiohydrolase.

11. A method for producing a cellulose degradable yeast, comprising the step of: co-introducing genes coding for at least three cellulose-degrading enzymes into a yeast host via integration with a yeast δ sequence, wherein the at least three cellulose-degrading enzymes are a combination of enzymes comprising (A) endoglucanase, (B) β-glucosidase, and (C) cellobiohydrolase, and wherein the ratio for genes of (A)/(B) is 2 or greater and the ratio for genes of (A)/(C) is greater than 1.

12. The method according to claim 11, wherein the combination of enzymes is a combination of endoglucanase, cellobiohydrolase, and β-glucosidase.

13. The method according to claim 11, wherein the cellulose-degrading enzymes are designed to be displayed on a cell surface.

14. The method according to claim 11, wherein the step of co-introduction is repeated twice or more.

15. The method of claim 11, wherein the enzymes are a combination of enzymes consisting of (A) endoglucanase, (B) β-glucosidase, and (C) cellobiohydrolase.

16. A method for producing a cellulose degradable yeast, comprising the step of:
co-introducing genes coding for at least two cellulose-degrading enzymes into a yeast host via cocktail δ integration with at least two vectors containing the respective cellulose-degrading enzymes between a pair of yeast δ sequences, wherein the at least two vectors have an identical yeast selectable marker, wherein the at least two cellulose-degrading enzymes are selected from a group consisting of endoglucanase, cellobiohydrolase, and β-glucosidase.

17. The method according to claim 16, wherein the at least two cellulose-degrading enzymes are a combination of enzymes that hydrolyze cellulose in different ways.

18. The method according to claim 17, wherein the combination of enzymes that hydrolyze cellulose in different ways is a combination of endoglucanase, cellobiohydrolase, and β-glucosidase.

19. The method according to claim 16, wherein the cellulose-degrading enzymes are designed to be displayed on a cell surface.

20. The method according to claim 16, wherein the step of co-introducing is repeated twice or more, and wherein the yeast selectable marker is different from that of the previous step of co-introducing.

* * * * *

```
                        SEQUENCE LISTING

<160> NUMBER OF SEQ ID NOS: 34

<210> SEQ ID NO 1
<211> LENGTH: 30
<212> TYPE: DNA
<213> ORGANISM: Artificial
<220> FEATURE:
<223> OTHER INFORMATION: Primer pPGKF(XhoI)

<400> SEQUENCE: 1
atatctcgag aaagatgccg atttgggcgc                                    30

<210> SEQ ID NO 2
<211> LENGTH: 36
<212> TYPE: DNA
<213> ORGANISM: Artificial
<220> FEATURE:
<223> OTHER INFORMATION: Primer pPGKR(SmaI)

<400> SEQUENCE: 2
atatcccggg gctagcgttt tatatttgtt gtaaaa                              36

<210> SEQ ID NO 3
<211> LENGTH: 48
<212> TYPE: DNA
<213> ORGANISM: Artificial
<220> FEATURE:
<223> OTHER INFORMATION: Primer tPGKF(SmaI)

<400> SEQUENCE: 3
atatcccggg tctagagaat tcagatctga aataaattga attgaatt                 48

<210> SEQ ID NO 4
<211> LENGTH: 32
<212> TYPE: DNA
<213> ORGANISM: Artificial
<220> FEATURE:
<223> OTHER INFORMATION: Primer tPGKR(NotI)

<400> SEQUENCE: 4
atatgcggcc gcagctttaa cgaacgcaga at                                  32

<210> SEQ ID NO 5
<211> LENGTH: 30
<212> TYPE: DNA
<213> ORGANISM: Artificial
<220> FEATURE:
<223> OTHER INFORMATION: Primer BGLF(XbaI)

<400> SEQUENCE: 5
atattctaga atgcaactgt tcaatttgcc                                     30

<210> SEQ ID NO 6
<211> LENGTH: 30
```

```
<212> TYPE: DNA
<213> ORGANISM: Artificial
<220> FEATURE:
<223> OTHER INFORMATION: Primer BGLR(XbaI)

<400> SEQUENCE: 6
atattctaga tttgattatg ttctttctat                                    30

<210> SEQ ID NO 7
<211> LENGTH: 30
<212> TYPE: DNA
<213> ORGANISM: Artificial
<220> FEATURE:
<223> OTHER INFORMATION: Primer CBHIIF(XbaI)

<400> SEQUENCE: 7
atattctaga atgcaactgt tcaatttgcc                                    30

<210> SEQ ID NO 8
<211> LENGTH: 30
<212> TYPE: DNA
<213> ORGANISM: Artificial
<220> FEATURE:
<223> OTHER INFORMATION: Primer CBHIIR(XbaI)

<400> SEQUENCE: 8
atattctaga tttgattatg ttctttctat                                    30

<210> SEQ ID NO 9
<211> LENGTH: 30
<212> TYPE: DNA
<213> ORGANISM: Artificial
<220> FEATURE:
<223> OTHER INFORMATION: Primer EGIIF(NheI)

<400> SEQUENCE: 9
atatgctagc atgcaactgt tcaatttgcc                                    30

<210> SEQ ID NO 10
<211> LENGTH: 30
<212> TYPE: DNA
<213> ORGANISM: Artificial
<220> FEATURE:
<223> OTHER INFORMATION: Primer EGIIR(SmaI)

<400> SEQUENCE: 10
atatcccggg tttgattatg ttctttctat                                    30

<210> SEQ ID NO 11
<211> LENGTH: 34
<212> TYPE: DNA
<213> ORGANISM: Artificial
<220> FEATURE:
<223> OTHER INFORMATION: Primer pPGKF(NotI)

<400> SEQUENCE: 11
atgcatgcgg ccgccgattt gggcgcgaat cctt                               34

<210> SEQ ID NO 12
<211> LENGTH: 50
<212> TYPE: DNA
<213> ORGANISM: Artificial
<220> FEATURE:
<223> OTHER INFORMATION: Primer tAGR(NotI)

<400> SEQUENCE: 12
ataagaatgc ggccgctttg attatgttct ttctatttga atgagatatg              50
```

<210> SEQ ID NO 13
<211> LENGTH: 30
<212> TYPE: DNA
<213> ORGANISM: Artificial
<220> FEATURE:
<223> OTHER INFORMATION: Primer 5'DSF(SacI)

<400> SEQUENCE: 13
atgcgagctc tgttggaata gaaatcaact                               30

<210> SEQ ID NO 14
<211> LENGTH: 40
<212> TYPE: DNA
<213> ORGANISM: Artificial
<220> FEATURE:
<223> OTHER INFORMATION: Primer 5'DSR(SacI)

<400> SEQUENCE: 14
gcatgagctc ggcgcgccat gtttatattc attgatccta                    40

<210> SEQ ID NO 15
<211> LENGTH: 40
<212> TYPE: DNA
<213> ORGANISM: Artificial
<220> FEATURE:
<223> OTHER INFORMATION: Primer 3'DSF(Kpn I)

<400> SEQUENCE: 15
atgcggtacc ggcgcgccat aaaatgatga taataatatt                    40

<210> SEQ ID NO 16
<211> LENGTH: 30
<212> TYPE: DNA
<213> ORGANISM: Artificial
<220> FEATURE:
<223> OTHER INFORMATION: Primer 3'DSR(KpnI)

<400> SEQUENCE: 16
gcatggtacc tgagaaatgg gtgaatgttg                               30

<210> SEQ ID NO 17
<211> LENGTH: 30
<212> TYPE: DNA
<213> ORGANISM: Artificial
<220> FEATURE:
<223> OTHER INFORMATION: Primer TRP1dF(Xho I)

<400> SEQUENCE: 17
atgcctcgag tggagtatgt ctgttattaa                               30

<210> SEQ ID NO 18
<211> LENGTH: 30
<212> TYPE: DNA
<213> ORGANISM: Artificial
<220> FEATURE:
<223> OTHER INFORMATION: Primer TRP1dR(XhoI)

<400> SEQUENCE: 18
gcatctcgag tgcaggcaag tgcacaaaca                               30

<210> SEQ ID NO 19
<211> LENGTH: 30
<212> TYPE: DNA
<213> ORGANISM: Artificial
<220> FEATURE:
<223> OTHER INFORMATION: Primer URA3dF(XhoI)

```
<400> SEQUENCE: 19
atgcctcgag gaaacgaaga taaatcatgt                                    30

<210> SEQ ID NO 20
<211> LENGTH: 30
<212> TYPE: DNA
<213> ORGANISM: Artificial
<220> FEATURE:
<223> OTHER INFORMATION: Primer URA3dR(XhoI)

<400> SEQUENCE: 20
cgatctcgag gtaataactg atataattaa                                    30

<210> SEQ ID NO 21
<211> LENGTH: 35
<212> TYPE: DNA
<213> ORGANISM: Artificial
<220> FEATURE:
<223> OTHER INFORMATION: Primer HIS3dF(Xho I)

<400> SEQUENCE: 21
accgtcgacc tcgagcttcg aagaatatac taaaa                              35

<210> SEQ ID NO 22
<211> LENGTH: 35
<212> TYPE: DNA
<213> ORGANISM: Artificial
<220> FEATURE:
<223> OTHER INFORMATION: Primer HIS3dR(Xho I)

<400> SEQUENCE: 22 gggcccccccc tcgagtcgag ttcaagagaa aaaaa                             35

<210> SEQ ID NO 23
<211> LENGTH: 20
<212> TYPE: DNA
<213> ORGANISM: Artificial
<220> FEATURE:
<223> OTHER INFORMATION: Primer BGL500-1000(F)

<400> SEQUENCE: 23
tcgtggcgac agccaagcat                                               20

<210> SEQ ID NO 24
<211> LENGTH: 20
<212> TYPE: DNA
<213> ORGANISM: Artificial
<220> FEATURE:
<223> OTHER INFORMATION: Primer BGL500-1000(R)

<400> SEQUENCE: 24
ggtacaggcg gtcgcggcca                                               20

<210> SEQ ID NO 25
<211> LENGTH: 20
<212> TYPE: DNA
<213> ORGANISM: Artificial
<220> FEATURE:
<223> OTHER INFORMATION: Primer EGII300-800(F)

<400> SEQUENCE: 25
cttgcgttac ctcgaaggtt                                               20

<210> SEQ ID NO 26
<211> LENGTH: 20
```

```
<212> TYPE: DNA
<213> ORGANISM: Artificial
<220> FEATURE:
<223> OTHER INFORMATION: Primer EGII300-800(R)

<400> SEQUENCE: 26
cagattgcca atcatttcca                                              20

<210> SEQ ID NO 27
<211> LENGTH: 20
<212> TYPE: DNA
<213> ORGANISM: Artificial
<220> FEATURE:
<223> OTHER INFORMATION: Primer CBHII300-800(F)

<400> SEQUENCE: 27
gttggggtca ctccttgggc                                              20

<210> SEQ ID NO 28
<211> LENGTH: 20
<212> TYPE: DNA
<213> ORGANISM: Artificial
<220> FEATURE:
<223> OTHER INFORMATION: Primer CBHII300-800(R)

<400> SEQUENCE: 28
catcgcaaca tttggaaggt                                              20

<210> SEQ ID NO 29
<211> LENGTH: 21
<212> TYPE: DNA
<213> ORGANISM: Artificial
<220> FEATURE:
<223> OTHER INFORMATION: Primer BGL 761F

<400> SEQUENCE: 29
cttccagggc tttgtgatgt c                                            21

<210> SEQ ID NO 30
<211> LENGTH: 20
<212> TYPE: DNA
<213> ORGANISM: Artificial
<220> FEATURE:
<223> OTHER INFORMATION: Primer BGL 858R

<400> SEQUENCE: 30
aggtgatatc gccaggcatt                                              20

<210> SEQ ID NO 31
<211> LENGTH: 21
<212> TYPE: DNA
<213> ORGANISM: Artificial
<220> FEATURE:
<223> OTHER INFORMATION: Primer EGII 694F

<400> SEQUENCE: 31
ccacggtcca agaggttgta a                                            21

<210> SEQ ID NO 32
<211> LENGTH: 20
<212> TYPE: DNA
<213> ORGANISM: Artificial
<220> FEATURE:
<223> OTHER INFORMATION: Primer EGII 774R

<400> SEQUENCE: 32
gccaatcatt tccaggcaaa                                              20
```

```
<210> SEQ ID NO 33
<211> LENGTH: 22
<212> TYPE: DNA
<213> ORGANISM: Artificial
<220> FEATURE:
<223> OTHER INFORMATION: Primer CBHII 571F

<400> SEQUENCE: 33
ggcgtcgcca aatataagaa ct                                                  22

<210> SEQ ID NO 34
<211> LENGTH: 21
<212> TYPE: DNA
<213> ORGANISM: Artificial
<220> FEATURE:
<223> OTHER INFORMATION: Primer CBHII 653R

<400> SEQUENCE: 34
ataaccagga gggtccggat a                                                   21
```